US010338003B2

(12) United States Patent
An et al.

(10) Patent No.: US 10,338,003 B2
(45) Date of Patent: Jul. 2, 2019

(54) APPARATUS FOR COUNTING TEXTILE CORDS OF TIRE REINFORCEMENT BELT

(71) Applicant: Hansung Sysco Co., Ltd., Yuseong-gu, Daejeon (KR)

(72) Inventors: Kwang Hee An, Daejeon (KR); Jun Sung Park, Seoul (KR)

(*) Notice: Subject to any disclaimer, the term of this patent is extended or adjusted under 35 U.S.C. 154(b) by 0 days.

(21) Appl. No.: 14/718,487

(22) Filed: May 21, 2015

(65) Prior Publication Data

US 2016/0327495 A1 Nov. 10, 2016

(30) Foreign Application Priority Data

May 8, 2015 (KR) .................. 10-2015-0064254

(51) Int. Cl.
*G01N 21/84* (2006.01)
*G01N 21/898* (2006.01)
*B29D 30/00* (2006.01)
*B29D 30/46* (2006.01)
*G06M 1/272* (2006.01)
*G01N 33/36* (2006.01)
*B29D 30/38* (2006.01)
(Continued)

(52) U.S. Cl.
CPC ..... *G01N 21/8983* (2013.01); *B29D 30/0061* (2013.01); *B29D 30/46* (2013.01); *G01N 33/36* (2013.01); *G06M 1/272* (2013.01); *B29D 2030/0066* (2013.01); *B29D 2030/381* (2013.01); *B29D 2030/463* (2013.01); *B29D 2030/466* (2013.01); *G01B 11/25* (2013.01); *G01N 2021/8927* (2013.01)

(58) Field of Classification Search
CPC .......... G01N 21/8915; G01N 21/8983; G01N 2021/8927; B29D 30/46; B29D 2030/463
USPC ........................................................ 356/430
See application file for complete search history.

(56) References Cited

U.S. PATENT DOCUMENTS 4,120,717 A * 10/1978 Rost ................... B29D 30/3007
156/395
4,475,815 A 10/1984 Takasu et al.
(Continued)

FOREIGN PATENT DOCUMENTS

EP 0374356 A2 6/1990
JP S6-3285453 11/1988
(Continued)

*Primary Examiner* — Sunghee Y Gray
(74) *Attorney, Agent, or Firm* — Lee & Associates, LLC; Jake K. Lee

(57) ABSTRACT

An apparatus for counting textile cords in a tire reinforcement belt by cutting the reinforcement belt into a plurality of belt units and successively measuring the number of textile cords in each belt unit is provided. The apparatus includes a feed roller having wound therearound a reinforcement belt on which textile cords are arranged along a longitudinal direction of the reinforcement belt; one or more take-up rollers configured to collect the reinforcement belt from the feed roller; a plurality of guide rollers interposed between the take-up rollers and configured to support a top surface or a bottom surface of the reinforcement belt; one or more light sources, each configured to emit a line of light onto a surface of the reinforcement belt that is passing around the guide rollers; and one or more image sensors configured to capture images reflected off the surface of the reinforcement belt.

3 Claims, 5 Drawing Sheets

(51) Int. Cl.
*G01N 21/892* (2006.01)
*G01B 11/25* (2006.01)

(56) References Cited

U.S. PATENT DOCUMENTS

| | | | | |
|---|---|---|---|---|
| 4,709,157 | A * | 11/1987 | Shimizu | G01N 21/8916 250/559.46 |
| 4,857,749 | A | 8/1989 | McCarty | |
| 5,095,214 | A * | 3/1992 | Eder | G01N 21/89 250/559.03 |
| 5,724,437 | A * | 3/1998 | Bucher | B41F 33/0036 101/183 |
| 2001/0027730 | A1 * | 10/2001 | Kamoda | B41F 33/0036 101/190 |
| 2003/0041763 | A1 * | 3/2003 | Riepenhoff | B41F 13/025 101/483 |
| 2004/0012786 | A1 * | 1/2004 | Hosel | G01N 21/8915 356/429 |
| 2004/0226465 | A1 * | 11/2004 | Morke | A24C 5/472 101/483 |
| 2005/0076993 | A1 | 4/2005 | Pialot | |
| 2005/0238565 | A1 * | 10/2005 | Sullivan | B82Y 30/00 423/447.1 |

FOREIGN PATENT DOCUMENTS

| | | |
|---|---|---|
| JP | 04-208892 | 7/1992 |
| JP | 05-256612 | 10/1993 |
| JP | 2006-167989 A | 6/2006 |
| JP | 2010-105204 A | 5/2010 |
| JP | 2011-196891 | 10/2011 |
| JP | 2012-106332 A | 6/2012 |
| JP | 2015-024518 A | 2/2015 |
| KR | 1020040090757 | 10/2004 |
| KR | 1020110011298 | 2/2011 |
| KR | 101198993 | 11/2012 |
| WO | 2012085632 A1 | 6/2012 |

* cited by examiner

APPARATUS FOR COUNTING TEXTILE CORDS OF TIRE REINFORCEMENT BELT

CROSS-REFERENCE TO RELATED APPLICATION(S)

This application claims priority from Korean Patent Application No. 10-2015-0064254, filed on May 8, 2015, in the Korean Intellectual Property Office, the disclosure of which is incorporated herein by reference in its entirety.

BACKGROUND

1. Field

The following description relates to an apparatus for counting textile cords of a tire reinforcement belt, and more specifically, to an apparatus for counting textile cords of a tire reinforcement belt, which cuts the reinforcement belt into a plurality of smaller belt units and successively counts the textile cords in each belt unit.

2. Description of the Related Art

Generally, to form a "green" tire, a reinforcement belt is wound around a belt material in a belt and tread assembly drum, wherein the reinforcement belt has arranged therein a plurality of textile cords that extend along the longitudinal direction of the reinforcement belt and are spaced apart from one another.

Before being wound over the belt material, the reinforcement belt needs to be checked as to whether textile cords are uniformly formed therein. Generally, X-ray equipment has been used to measure the number of textile cords in the reinforcement belt.

Such X-ray equipment used in the existing apparatuses for counting textile cords is pricey. In addition, using the X-ray equipment does not enable real-time inspection, and thus the X-ray equipment needs to be paused and reactivated each time X-ray inspection is performed, which results in an increase in the total manufacturing time of the reinforcement belt and a degradation of productivity.

PRIOR ART DOCUMENT(S)

Patent Application Document

1. Korean Patent No. 10-1198993

SUMMARY

In one general aspect, there is provided an apparatus for counting textile cords of a tire reinforcement belt, the apparatus including: a feed roller having wound therearound a reinforcement belt on which a plurality of textile cords are arranged along a longitudinal direction of the reinforcement belt; one or more take-up rollers configured to collect the reinforcement belt rolled out from the feed roller; a plurality of guide rollers interposed between the take-up rollers and configured to support a top surface or a bottom surface of the reinforcement belt rolled out from the feed roller; one or more light sources, each configured to emit a line of light onto a surface of the reinforcement belt that is passing around the guide rollers; and one or more image sensors configured to capture images reflected off the surface of the reinforcement belt.

Other features and aspects will be apparent from the following detailed description, the drawings, and the claims.

Figure 1:
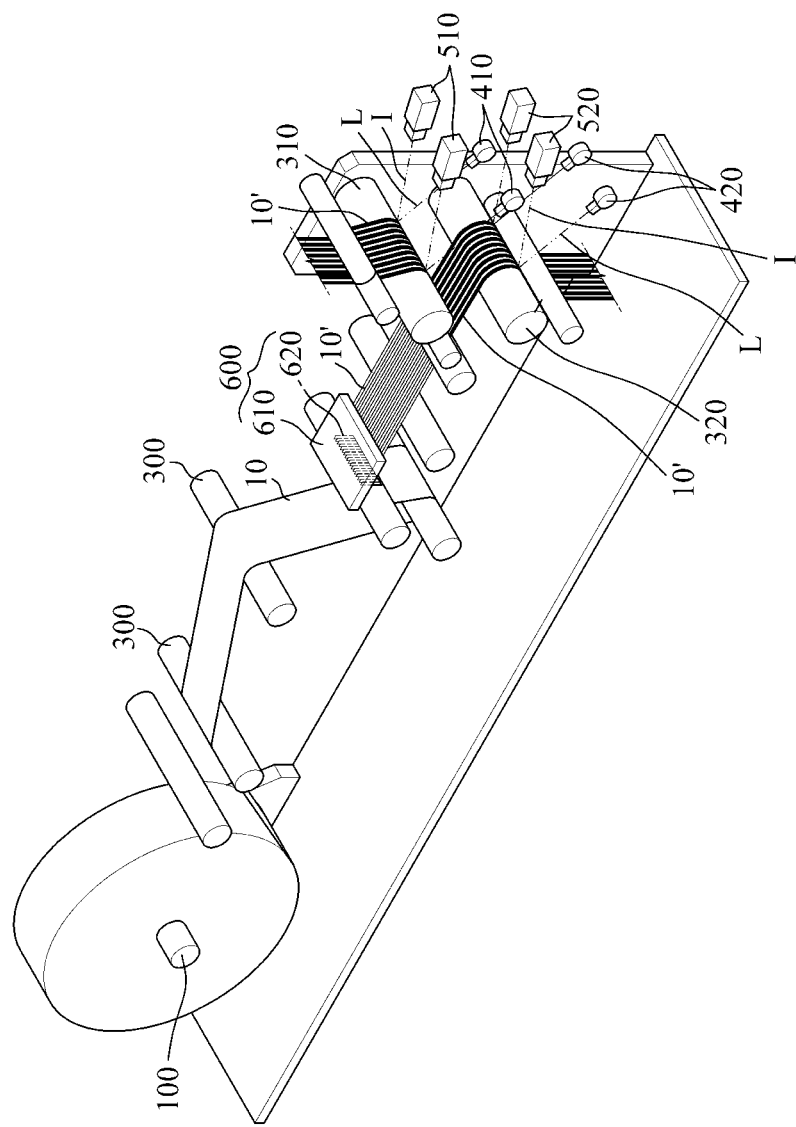
FIG. 1 is a perspective view of an apparatus for counting the number of textile cords of a tire reinforcement belt according to an exemplary embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following description is provided to assist the reader in gaining a comprehensive understanding of the methods, apparatuses, and/or systems described herein. Accordingly, various changes, modifications, and equivalents of the methods, apparatuses, and/or systems described herein will be suggested to those of ordinary skill in the art. Also, descriptions of well-known functions and constructions may be omitted for increased clarity and conciseness.

Figure 2:
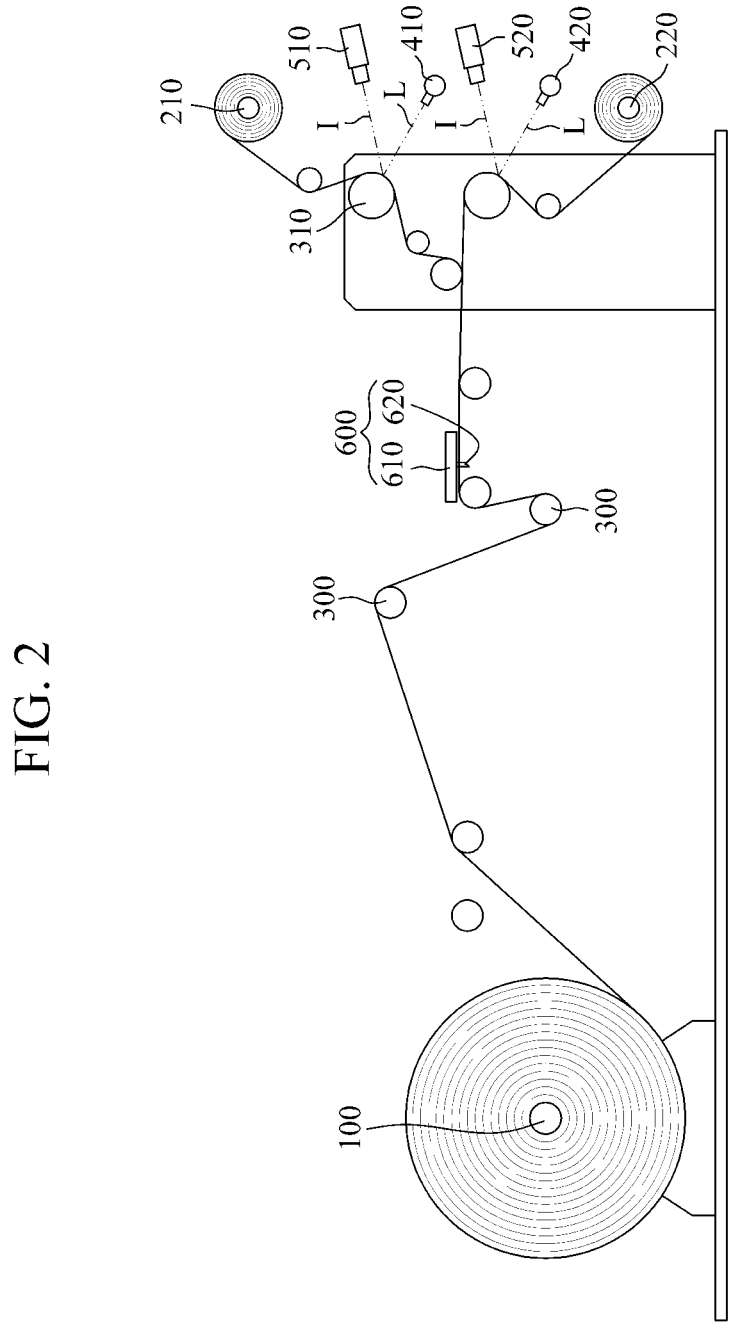
FIG. 2 is a side view of the apparatus of FIG. 1.

An apparatus for counting textile cords in a tire reinforcement belt cuts the reinforcement belt into a plurality of smaller belt units and successively measures the number of textile cords in each belt unit, and FIG. 1 and FIG. 2 illustrate an exemplary embodiment of the apparatus.

FIG. 1 is a perspective view of an apparatus for counting textile cords of a tire reinforcement belt according to an exemplary embodiment. FIG. 2 is a side view of the apparatus of FIG. 1.

The apparatus for counting textile cords of a tire reinforcement belt includes a feed roller 100 around which a reinforcement belt 10 is wound, the reinforcement belt 10 having embedded therein, a number of spaced apart textile cords 20 extending along a longitudinal direction of the belt 10; one or more take-up rollers 210 and 220 around which the reinforcement belt 10 that has rolled out from the feed roller 100 is re-wound; a plurality of guide rollers 310 and 320 that are interposed between the feed roller 100 and the take-up rollers 210 and 220 and support either a top surface or a bottom surface of the reinforcement belt 10 to keep in tension the reinforcement belt 10 rolled out from the feed roller 100; light sources 410 and 420 that emit a line of light L, such as laser, onto a surface of the reinforcement belt 10 that is passing around the guide rollers 310 and 320; and image sensors 510 and 520 that capture images I reflected off the surface of the reinforcement belt 10.

The reinforcement belt 10 is wound over a belt material of a tire and has embedded therein a number of spaced-apart textile cords 20 extending along a longitudinal direction thereof.

The reinforcement belt 10 with a designated width is wound around the feed roller 100, and it is rolled out from one side of the feed roller 100.

The reinforcement belt 10 rolled out from the feed roller 100 is re-wound around one or more take-up rollers 210 and 220. The take-up rollers 210 and 220 are shaft connected to separate rotation driving means, such as motors, and are rotated thereby, and at this time, the reinforcement belt 10 rolled out from the feed roller 100 is re-wound around the take-up rollers 210 and 220.

The guide rollers 310 and 320 are interposed between the feed roller 100 and the take-up rollers 210 and 220 and support the top surface or the bottom surface of the reinforcement belt 10 to keep the tension of the belt 10. One or more guide rollers 310 and 320 may be provided, which may keep the reinforcement belt 10 in tension while the belt 10 is traveling from the feed roller 100 to the take-up rollers 210 and 220.

The light sources 410 and 420 emits a line of light L, such as laser, onto a surface of the reinforcement belt 10 that is passing around the guide rollers 310 and 320, and various embodiments of relevant elements, such as laser emission means, may be made as long as the embodiment emits a line of light L in a direction parallel to the width direction of the reinforcement belt 10.

The image sensors 510 and 520 capture images I reflected off the surface of the reinforcement belt 10.

As described above, a number of textile cords 20 spaced apart from each other are arranged inside the reinforcement belt 10 along the longitudinal direction of the reinforcement belt 10. At this time, the textile cords 20 make the surface of the reinforcement belt 10 wavy. That is, projections 10a are formed on the exterior surface of the reinforcement belt 10 along the longitudinal direction of the belt 10 due to the thickness of the textile cords 20 and the remaining portion of the belt 20 has formed thereon grooves 10b.

Thus, the number of textile cords 20 can be measured by counting the protrusions in the images of the surface of the reinforcement belt 10 which are obtained by the light sources 410 and 420 and the image sensors 510 and 520.

For the aforementioned operation, the images obtained by the image sensors 510 and 520 are transferred to a reader, and the reader counts the number of textile cords 20 of the reinforcement belt 10 and detects a defect in the textile cords.

Methods for measuring the numbers of projections 10a and grooves 10b based on the obtained images are well-known techniques, and thus detailed descriptions thereof will be omitted.

The image sensors 510 and 520 may be arranged coaxially with the respective light sources 410 and 420, or be arranged to form an angle relative to the respective light sources 410 and 420, the light source 410 and 420 each emit a line of light L onto the surface of the reinforcement belt 10, and then the image sensors 510 and 520 capture images I reflected off the surface of the reinforcement belt 10.

Figure 5:
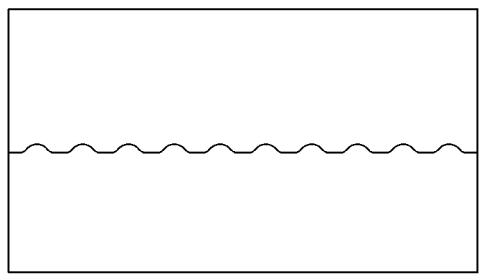
FIG. 5 is a diagram illustrating an example of an image obtained by an image sensor.

At this time, the straight line of light L emitted from each light source 410 and 420 is reflected in the shape of the surface of the reinforcement belt 10, and it may appear as a wavy line as shown in FIG. 5.

In addition, the line of light L emitted from each light source 410 and 420 may be projected onto the surface of the reinforcement belt 10 after passing through a separate collimator lens for rendering a parallel beam of light.

In another exemplary embodiment, a plurality of light sources 410 and 420 and a plurality of image sensors 510 and 520 may be arranged along a width direction of the reinforcement belt 10.

Because it is difficult to acquire an image of the entire width of the reinforcement belt 10 with only one light source 410 or 420 and one image sensor 510 or 520, and even if acquired, the obtained image may not be of a high resolution, a number of light sources 410 and 420 and a number of image sensors 510 and 520 are arranged along a width direction of the reinforcement belt 10, so that each of the light sources 410 and 420 and each of the image sensors 510 and 520 can obtain an image of a corresponding portion of the reinforcement belt 10, allowing for the inspection of the number of textile cords 20 in said portion.

Figure 3:
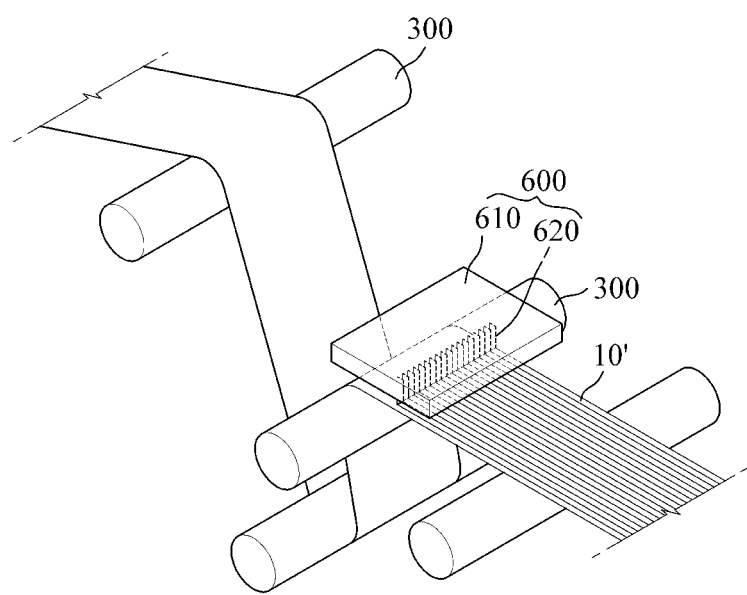
FIG. 3 is a perspective view of a portion of the apparatus of FIG. 1 where the reinforcement belt is passing through a cutting component.

FIG. 3 is a perspective view of a portion of the apparatus of FIG. 1 where the reinforcement belt is passing through a cutting component.

In one exemplary embodiment, the apparatus includes a cutting component 600 to cut the reinforcement belt 10 from the feed roller 100 into a number of smaller belt units 10' and pass the belt units 10' therethrough.

The cutting component 600 may consist of a frame 610 formed to be placed above the reinforcement belt 10 and a plurality of cutters 620 that protrude downward to a given length from a bottom surface of the frame 610 to cut the reinforcement belt 10 when the belt 10 is passing under the frame 610. The plurality of cutters 620 are disposed along the width direction of the reinforcement belt 10, and cut the reinforcement belt 10 that is passing under the frame 610 into the smaller belt units 10' and output them.

Figure 4:
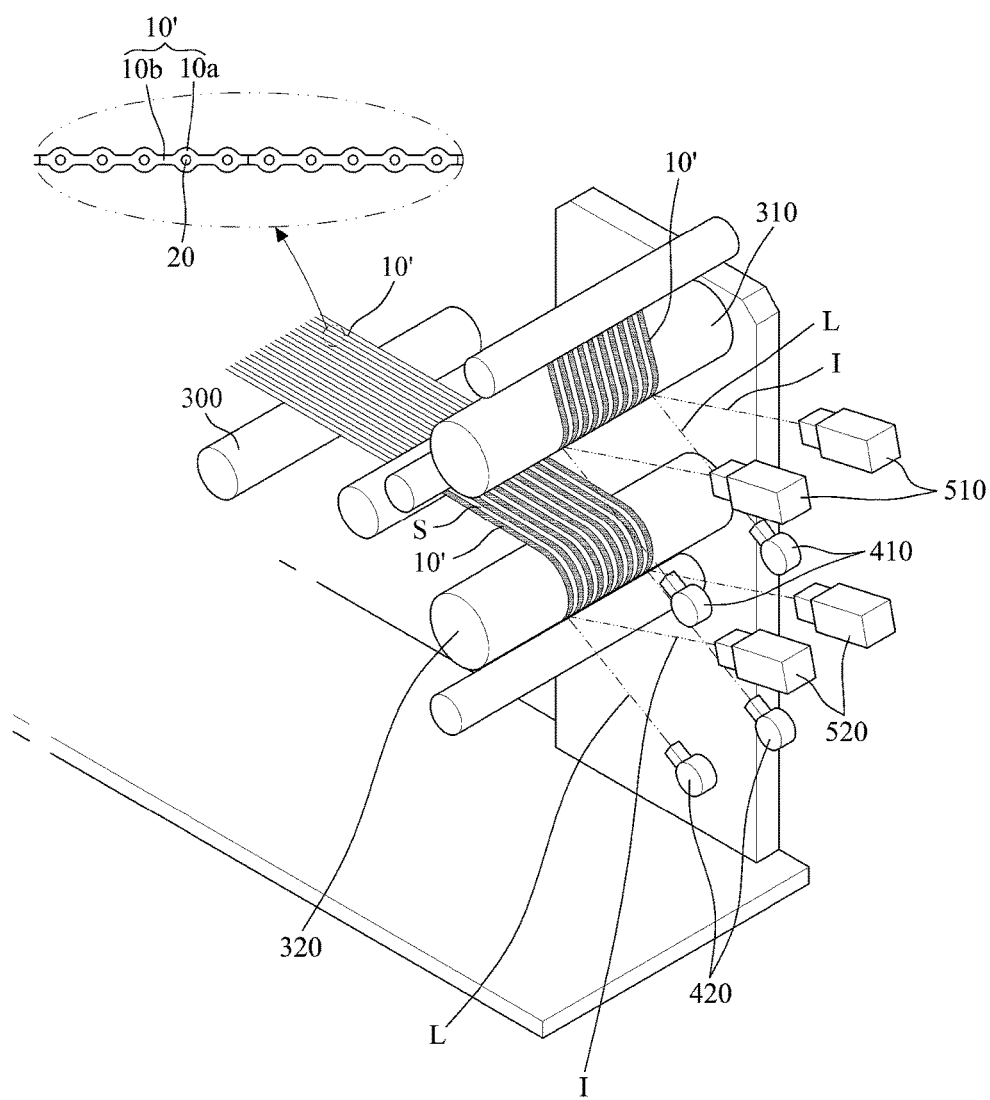
FIG. 4 is a perspective view of a portion of the apparatus of FIG. 1 where belt units that have passed through the cutting component are alternately transferred to an upper part and to a lower part.

FIG. 4 is a perspective view of a portion of the apparatus of FIG. 1 where each of the belt units that have passed through the cutting component is alternately transferred to an upper part and to a lower part of the apparatus.

In one exemplary embodiment, each of the plurality of belt units 10' that have passed through the cutting component 600 is collected by either take-up roller A 210 which is placed above the cutting component 600 or take-up roller B 220 which is placed below the cutting component 600, and the subsequently fed belt unit 10' is collected by the other take-up roller 210 or 220.

For example, odd-numbered belt units 10' are collected by take-up roller B 220 positioned below the cutting component 600 and even-numbered belt units 10' are collected by take-up roller A 210 positioned above the cutting component 600.

When each of the unit belts 10' is transferred alternately to an upper part and a lower part and collected alternately by the take-up rollers A or B 210 and 220, there will be formed a space S between the belt units 10', whereby the belt units 10' fed into the take-up rollers A and B 210 and 220 can be clearly distinguished from each other.

In one exemplary embodiment, each of the plurality of belt units 10' that have passed through the cutting component 600 is re-wound in tension around either take-up roller A 210 or take-up roller B 220, as passing around either guide roller A 310 in the upper or lower guide roller B 320 in the lower.

In one exemplary embodiment, the light sources 410 and 420 may consist of light source A 410 that emits a line of light L at an angle relative to a surface of each belt unit 10' that is passing around the guide roller A 310 and light source B 420 that emits a line of light L at an angle relative to a surface of each belt unit 10' that is passing around the guide roller B 320. The image sensors 510 and 520 may consist of image sensor A 510 that captures an image I reflected off a surface of each belt unit 10' that is passing around the guide roller A 310 and image sensor B 510 that captures an image reflected off a surface of each belt unit 10' that is passing around the guide roller B 320.

That is, the light source A 410 emits a line of light L to the surface of belt unit 10' that is passing around the guide roller A 310, and the image sensor A 510 acquires the image I reflected off said belt unit 10'.

In addition, the light source B 420 emits a line of light L to the surface of belt unit 10' that is passing around the guide roller B 320, and the image sensor B 520 acquires the image reflected off said belt unit 10'.

When each of the unit belts 10' is transferred alternately to an upper part and a lower part, one that is transferred upward passes around the guide roller A 310 and is collected by the take-up roller A and the other that is transferred downward passes through the guide roller B 320 is collected by the take-up roller B 220, so that there will be formed a space S between the belt units 10', whereby the belt units 10' fed into the take-up rollers A and B 210 and 220 can be clearly distinguished from each other. Therefore, it is possible for the image sensor A 510 and the image sensor B 520 to acquire images of each belt unit 10' and measure the number of textile cords 20 in each image of the belt unit 10'.

According to the exemplary embodiments described above, a reinforcement belt is cut into a plurality of smaller belt units and successive counting of textile cords provided in each belt unit is possible, so that the manufacturing time is reduced.

In addition, the belt units cut from the reinforcement belt are transferred alternately to an upper part and a lower part and automatically collected by two take-up rollers, so that it is possible to reduce the operation time for separating the belt units, thereby increasing the workability.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for counting textile cords of a tire reinforcement belt, the apparatus comprising:
    a feed roller having wound therearound a reinforcement belt on which a plurality of textile cords are arranged along a longitudinal direction of the reinforcement belt;
    two or more take-up rollers configured to collect the reinforcement belt rolled out from the feed roller;
    a plurality of guide rollers interposed between the take-up rollers and configured to support a top surface or a bottom surface of the reinforcement belt rolled out from the feed roller;
    one or more light sources, each configured to emit a line of light onto a surface of the reinforcement belt that is passing around the guide rollers;
    one or more image sensors configured to capture images reflected off the surface of the reinforcement belt; and
    a cutting component configured to cut the reinforcement belt into a plurality of smaller belt units and pass the belt units therethrough,
    wherein each of the plurality of belt units having passed through the cutting component is transferred to either take-up roller A at an upper position or take-up roller B at a lower position, wherein when one belt unit is collected by either the take-up roller A or the take-up roller B, a following belt unit is collected by the other take-up roller.

2. The apparatus of claim 1, wherein each of the plurality of belt units that have passed through the cutting component passes around either guide roller A at an upper position and guide roller B at a lower position and the belt units passing around the guide roller A are re-wound around the take-up roller A and the other belt units passing around the guide roller B are re-wound around the take-up roller B.

3. The apparatus of claim 2, wherein the light sources comprise a light source A to emit a line of light at an angle relative to the surface of the belt unit that is passing around the guide roller A and light source B to emit a line of light at an angle relative to the surface of the belt unit that is passing around the guide roller B, and the image sensors comprise image sensor A to capture the image reflected off the surface of the belt unit that is passing around the guide roller A and image sensor B to capture the image reflected off the surface of the belt unit that is passing around the guide roller B.

* * * * *